United States Patent
Wessig et al.

(10) Patent No.: US 7,514,540 B2
(45) Date of Patent: *Apr. 7, 2009

(54) FUNCTIONALIZED CARRIER MATERIAL CONTAINING COVALENTLY BOUND BIOMOLECULE VIA A LINKER

(75) Inventors: Pablo Wessig, Berlin (DE); Jürgen Bendig, Berlin (DE); Uwe Schedler, Berlin (DE)

(73) Assignee: Poly-An Gesellschaft zur Herstellung Von Polymeren Fuer Spezielle Anwendungen und Analytik mbH, Berlin (DE)

( * ) Notice: Subject to any disclaimer, the term of this patent is extended or adjusted under 35 U.S.C. 154(b) by 731 days.

This patent is subject to a terminal disclaimer.

(21) Appl. No.: 10/451,652

(22) PCT Filed: Dec. 3, 2001

(86) PCT No.: PCT/EP01/14072

§ 371 (c)(1),
(2), (4) Date: Jan. 22, 2004

(87) PCT Pub. No.: WO02/051872

PCT Pub. Date: Jul. 4, 2002

(65) Prior Publication Data

US 2004/0132149 A1    Jul. 8, 2004

(30) Foreign Application Priority Data

Dec. 22, 2000  (DE) .............................. 100 65 787

(51) Int. Cl.
C07K 1/00     (2006.01)
C07K 17/14    (2006.01)
C07K 17/10    (2006.01)
C07K 17/08    (2006.01)
C07K 17/06    (2006.01)
C12N 11/14    (2006.01)
C12N 11/10    (2006.01)
C12N 11/06    (2006.01)

(52) U.S. Cl. ...................... 530/402; 435/176; 435/178; 435/181; 530/811; 530/813; 530/816

(58) Field of Classification Search .................... None
See application file for complete search history.

(56) References Cited

U.S. PATENT DOCUMENTS 5,071,529 A    12/1991   Horn ........................ 204/157.6
5,389,533 A     2/1995   von Gentzkow et al. .... 435/180
5,853,744 A    12/1998   Mooradian et al. .......... 424/422

OTHER PUBLICATIONS

Kieser et al., 'Cyclopeptide derivatives for molecular recognition,' Proc. SPIE, 4205:75-83 (2001).
Clémence et al., 'Photoimmobilization of a Bioactive Laminin Fragment and Pattern-Guided Selective Neuronal Cell Attachment,' Bioconjugate Chem., 6:411-7 (1995).

*Primary Examiner*—David M Naff
(74) *Attorney, Agent, or Firm*—Kriegsman & Kriegsman

(57) ABSTRACT

The invention concerns a method for immobilizing biomolecules on a polymeric surface of a carrier material and a carrier material functionalized with a biomolecule according to the general formulas (IV) and (V), which can be produced according to the method, wherein P indicates the polymeric surface of the carrier material and M indicates the biomolecule bound to the linker compound via an amino group (formula IV) or a carbonyl group (formula V) and $R^2$ has the meaning $OR^4$ or $NR^4R^5$; $R^1$, $R^4$ and $R^5$, independently of one another, indicate H, and alkyl group or an aryl group; $R^3$ indicates H, an alkyl, an aryl, an acyl, an alkoxycarbonyl or an aryloxycarbonyl group; and the alkyl, aryl, acyl, alkoxycarbonyl and/or aryloxycarbonyl group of the radicals $R^1$, $R^3$, $R^4$ and $R^5$, independently of one another, are substituted or unsubstituted.

10 Claims, 2 Drawing Sheets

(I)

(IV)

(V)

FUNCTIONALIZED CARRIER MATERIAL CONTAINING COVALENTLY BOUND BIOMOLECULE VIA A LINKER

BACKGROUND OF THE INVENTION

1. Field of the Invention

The invention concerns a method for immobilizing biomolecules to a carrier material, a carrier material functionalized with a biomolecule as well as the use thereof.

2. Description of Related Art

The binding of biomolecules, particularly proteins or peptides, but also complex molecules with peptide structural units and amino acids to carrier materials, the so-called solid phase, is known for pursuing different objectives. The carrier materials are insoluble under the specified, usually aqueous, solution conditions. Such a carrier material functionalized with a biomolecule is used in order to fix, concentrate, and/or separate other biomolecules, usually also amino acids, peptides, proteins or complex molecules or supramolecular systems with peptidic structural units. According to the concept of the antigen-antibody reaction, these molecules form specific and structurally-selective complexes with the immobilized biomolecule with the formation of non-covalent van-der-Waals bonds and hydrogen bonds. Thus, peptide units and peptidic secondary structural elements are recognized as receptor units (U. Diederichsen, et al., Bioorganic Chemistry, Wiley Publishing Co. Chemistry, Weinheim 1999, pp. 221 ff; G. Gauglitz et al., Proc. SPIE 4205: Advanced Environmental and Chemical Sensing Technology, 2000, 10).

The biomolecule can be immobilized on the carrier material by physical adsorption, whereby the binding forces that participate are primarily hydrogen bonds and van-der-Waals forces, or by ionic bonding based on electrostatic forces or by covalent bonding by chemical reaction. The covalent immobilization of biomolecules is usually conducted on polymeric carrier materials or carrier materials which have a polymeric surface. For covalent bonding, it is also known to provide the biomolecule with functional groups that can be readily activated, which can enter into a chemical bond with the carrier material. By introducing the energy necessary for the chemical reaction by heating or exposing with energy-rich radiation, reactive intermediates are formed from the functional group of the biomolecule, which then react with the polymer surface and immobilize the amino acid, the peptide, the protein or the complex molecule with peptidic structure by way of covalent bonding.

In this context, WO 91/16425 as well as U.S. Pat. No. 5,853,744 describe the use of azide-derivatized biomolecules, which form nitrenes with cleavage of nitrogen upon heating or by photolysis, which in turn react with polymer surfaces particularly by combined abstraction and insertion reactions and [are] immobilize[d] together with the biomolecule as an amine. WO 91/16425 as well as Clemence et al. (Bioconjugate Chem., 1995, 6, 411-417) describe further the derivatising of biomolecules with diaziridine functions, which covalently bind to the polymer surface after activation and subsequent three-ring opening. In addition, EP 562,373 A discloses the use of epoxy-derivatized polymeric carriers for covalent bonding of biochemical substances.

It is also known to use the sensitizer capacity of benzophenone structures relative to the photochemical H or proton abstraction (both H+ as well as H°) with subsequent recombination of the intermediate radicals for immobilizing amino acids and peptides. In this way, the receptor units (amino acid, peptide) to be immobilized are additionally provided with a benzophenone structure. When this conjugate is photochemically excited in the vicinity of a polymer surface, H or proton abstraction (both H+ as well as H°) from the polymer or from the peptide is bound by the excited benzophenone results, with the formation of radicals on the part of the polymer and/or the peptide, which then enter into combination reactions. In the course of these radical combinations, the functionalized receptor unit to be bound to the polymer is at least partially covalently bound to the surface of the polymer and thus the biomolecules is immobilized (M. Ulbricht et al., J. Membr. Sci. 1996, 120, 239-259; U.S. Pat. No. 5,071,529; J.-F. Clemence et al., Bioconjugate Chem. 1995, 6, 411-417).

SUMMARY OF THE INVENTION

The object of the invention is to provide a novel method for immobilizing biomolecules, which is characterized by a high reliability and a good yield, which can be conducted under mild conditions and offers a high variability with respect to the carrier materials and biomolecules that can be utilized. It will also provide a carrier material functionalized with a biomolecule that can be produced by the method.

The first aspect of this object is solved by a method with the features of claim 1. The method according to the invention for immobilizing biomolecules, particularly amino acids, peptides, proteins or molecules with at least one peptidic structural unit, comprises the steps:

(a) Reacting the biomolecule to be immobilized with a linker compound according to the general formula (I):

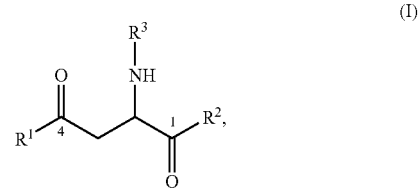

with the formation of a covalent bond between the biomolecule and the C1 position or the amino group of the linker compound, whereby $R^2$ has the meaning $OR^4$ or $NR^4R^5$;

$R^1$, $R^4$ and $R^5$, independently of one another, indicate H, an alkyl group or an aryl group; $R^3$ indicates H, an alkyl, an aryl, an acyl, an alkoxycarbonyl or an aryloxycarbonyl group; and the alkyl, aryl, acyl, alkoxycarbonyl and/or aryloxycarbonyl group of the radicals $R^1$, $R^3$, $R^4$ and $R^5$, independently of one another, are substituted or unsubstituted;

(b) Introducing the biomolecule bound with the linker compound onto a polymeric surface of a carrier material; and (c) Irradiating the surface with light of the UV-vis spectral region with the formation of a covalent bond between the C4 position of the linker compound and the polymeric surface.

The linker compound according to the invention in its simplest structure can be based on a glycine, which is derivatized at its $C^\alpha$ position with a 2-oxo-ethyl unit by means of which the covalent binding to the carrier material is finally produced. Thus, depending on the selection of the radicals $R^2$ and $R^3$, two functional groups are produced for the binding of the biomolecule to be immobilized.

According to a preferred embodiment of the method, the covalent bond between the biomolecule and the linker compound is a peptide bond, which is formed selectively either between the N terminal of the biomolecule and the C1 position of the linker compound and/or between the C terminal of the biomolecule and the amino group of the linker compound.

If a selective N or C-terminal binding of the biomolecule to the linker compound is desired, this can be controlled by blocking the N terminal or the C terminal of the biomolecule and/or the C1 position or the amino group of the linker compound with chemical protective groups. The use of chemical protective groups for the region-specific conducting of the reaction is familiar to the person skilled in the art. Thus, for example, with respect to the biomolecule, a protection of an N-terminal amino group is achieved by introducing a tert-butoxycarbonyl group (Boc). Subsequent to the reaction with the linker compound, the Boc group can then be removed again from the amino group by hydrolysis. With respect to the linker compound, the coupling of the biomolecule can be controlled by suitable selection of the radicals $R^2$ or $R^3$, whereby the amino function can also be protected by a Boc group.

Organic polymers are particularly suitable as the carrier material and/or the polymeric surface of the carrier material. These include, in particular, polypropylene, polyethylene, polysulfone, polyether sulfone, polystyrene, polyvinyl chloride, polyacrylonitrile, cellulose, amylose, agarose, polyamide, polyimide, polytetrafluoroethylene, polyvinylidene difluoride, polyester, polycarbonate, polyacrylate, polyacrylamide or derivatives of these or a copolymer or a blend thereof. In addition, inorganic and/or mineral materials can also be utilized as the carrier material, particularly glass, silicates, ceramic materials or metal. In addition, the use of composites comprised of at least one inorganic and/or mineral material and at least one organic polymer is conceivable. In the case of pure inorganic and/or mineral carrier materials, a coating with one of the named organic polymer materials may be necessary in order to make binding possible.

With respect to its external configuration, the carrier material can be present in the form of a membrane, a film, a plate, a microtiter plate, a test tube, a glass slide, a fiber, a hollow fiber, a nonwoven material, a woven fabric, a powder, a granulate or in the form of particles. Thus, the carrier material may have a porous or nonporous structure. It is most preferably provided that the carrier material is present in the form of a membrane with a symmetrical or asymmetrical pore structure, whereby the pore size can lie in the range of 1 nm to 10 µm.

The linker compound according to formula (II) is introduced onto the carrier material or its polymeric surface, by impregnating, moistening or coating, depending on the external shape of the carrier material.

The surface can be exposed—although this is not absolutely necessary—particularly advantageously in the presence of a sensitizer. The yield of the photoreaction can be increased in this way. Irradiation is preferably conducted with light of the wavelength region of 250 to 500 nm. The selection of the wavelength or the wavelength region used primarily depends on the radical $R^1$, the polymeric surface and the presence and the type of sensitizer. Suitable light sources, for example, are lasers, UV tubes or mercury vapor lamps, whereby the wavelength region can be limited optionally by the use of suitable filters. The light-induced coupling of molecules to polymeric surfaces is known, for example, from WO 91/16425 or EP 0 562,373 A2 and shall not be explained in more detail here.

After the photochemical conversion has been produced, unreacted linker compound, by-products and, optionally, the sensitizer can be removed by washing with water, an organic solvent or a solvent mixture, and the functionalized carrier material is dried. The dried product is very stable and can be stored at room temperature for weeks and months.

The object on which the invention is based is also solved by a functionalized carrier material with the features of claim 19. The functionalized carrier material comprises a polymeric surface and at least one biomolecule according to the general formula (IV) or (V), which is covalently bound to the surface via a linker compound:

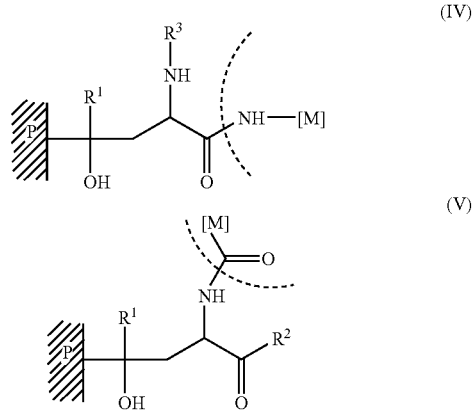

in which P indicates the polymeric surface of the carrier material and M indicates the biomolecule bound to the linker compound via an amino group (formula IV) or a carbonyl group (formula V) and $R^2$ has the meaning $OR^4$ or $NR^4R^5$; $R^1$, $R^4$ and $R^5$, independently of one another, indicate H, an alkyl group or an aryl group; $R^3$ indicates H, an alkyl, an aryl, an acyl, an alkoxycarbonyl or an aryloxycarbonyl group; and the alkyl, aryl, acyl, alkoxycarbonyl and/or aryloxycarbonyl group of the radicals $R^1$, $R^3$, $R^4$ and $R^5$, independently of one another, are substituted or unsubstituted.

The functionalized carrier material comprises accordingly an immobilized biomolecule, which is covalently bonded to the polymeric surface of the carrier material via an optionally substituted 1-oxo-2-amino-4-hydroxybutyl unit. Thus, the biomolecule is peptidically bound either via its amino group to the C1 carbonyl function of the linker compound or via its carbonyl group to the amino function of the linker compound.

In principle, the biomolecule may involve any molecule, which makes available an amino function and/or a terminal carbonyl or carboxyl function suitable for the coupling. Most preferably, the biomolecule involves an amino acid, a peptide, a protein or a complex molecule with at least one peptidic structural unit.

The functionalized carrier material according to the invention can be used particularly advantageously for the concentration, separation and/or fixation of other amino acids, peptides, proteins or more complex molecules with peptidic structural units.

Other preferred embodiments of the invention result from the other features named in the subclaims.

DETAILED DESCRIPTION OF THE INVENTION

The invention will be explained in further detail below in examples of embodiment.

Figure 3:
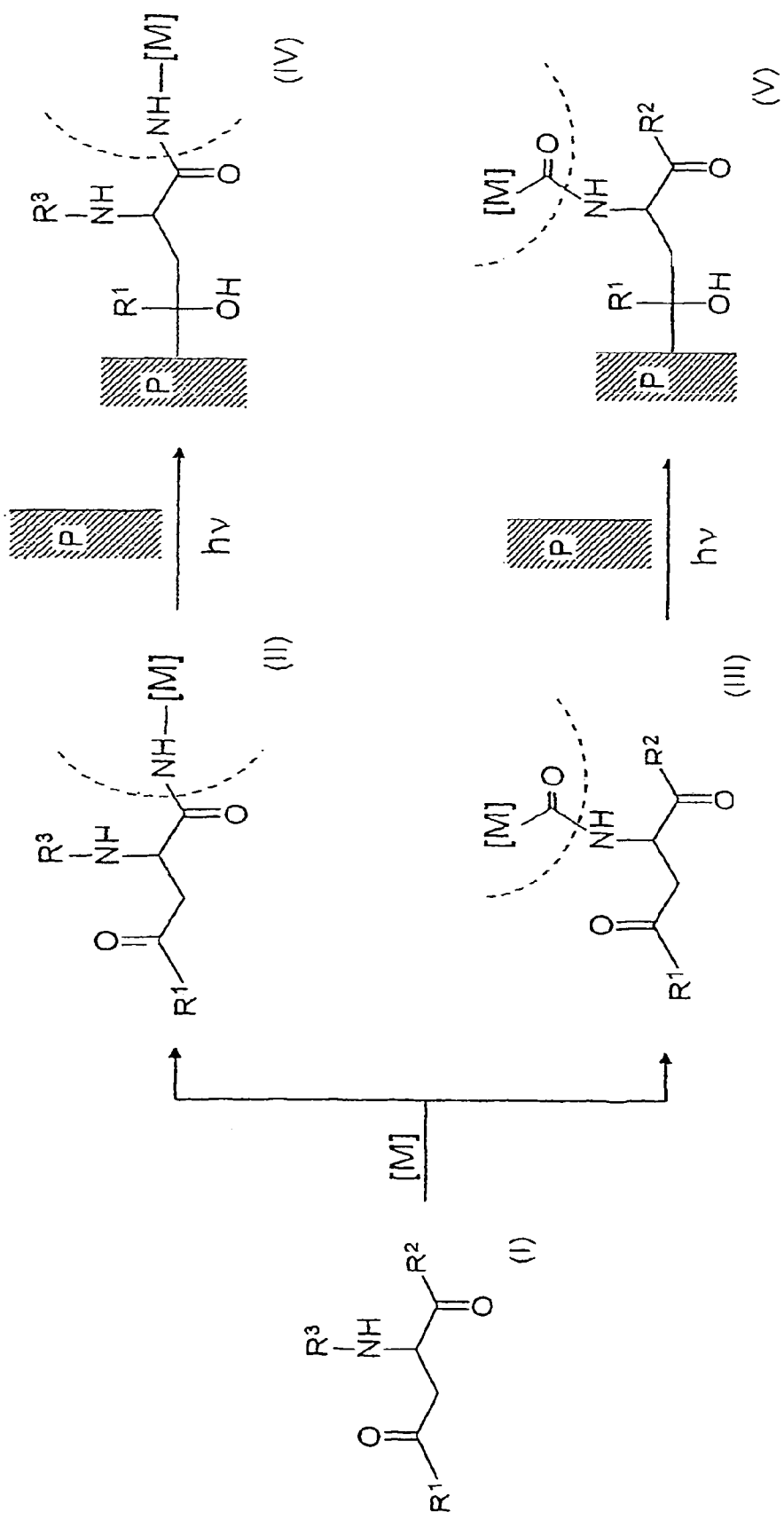
FIG. 3 shows an overview of the steps of a method for immobilizing biomolecules onto a polymeric surface of a carrier material resulting in a functionalized carrier material according to the present invention.

FIG. 3 first shows a schematic overview of the immobilization method according to the invention. The linker compound according to formula (I) is converted in a first step with a biomolecule M, for example, a peptide. Two types of binding are possible. First of all, the binding can be produced via an amino group of the biomolecule, roughly the N terminal, to the C1 carbonyl position of the linker compound (I) with the formation of the compound according to the general formula (II). Alternatively or parallelly thereto, corresponding to the lower branch of the figure, the binding can be produced via a carbonyl or carboxyl group of the biomolecule, particularly the C terminal, to the amino group of the linker compound, from which a compound according to formula (III) results. As already explained, a region-specific control can be produced by use of chemical protective groups for each of the functions of the linker compound and/or of the biomolecule that are not to be bound. In a subsequent step, the compound according to formula (II) and/or (III) is introduced onto a polymeric surface P of a carrier material, for example, a membrane, and irradiated with light of a suitable wavelength. A covalent bond is formed between the linker compound and the surface, with the production of a carrier material functionalized with the biomolecule, according to formula (IV) and/or (V).

EXAMPLE 1

Figure 1:
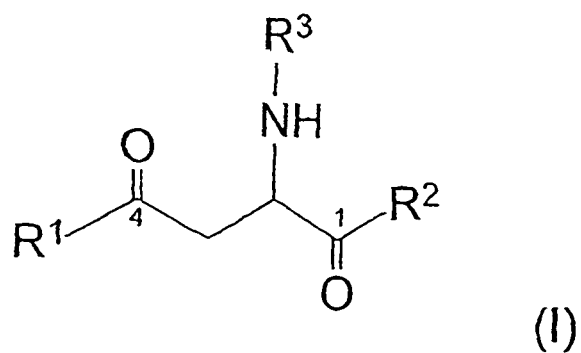
FIG. 1 shows a linker compound used for immobilizing biomolecules onto a polymeric surface of a carrier material.
Figure 2:
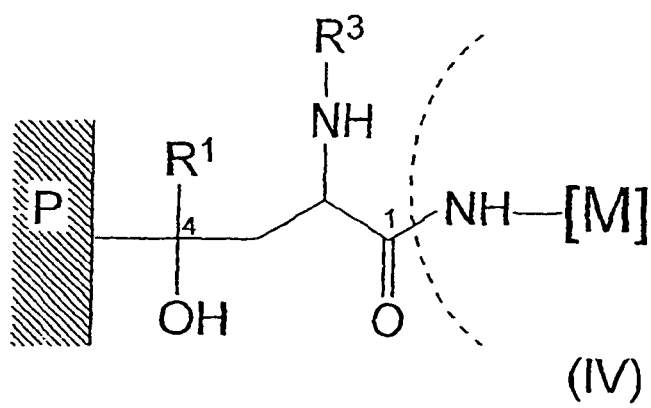
FIG. 2 shows two alternative structures of a carrier material according to the present invention which is functionalized with a biomolecule.
Figure 2:
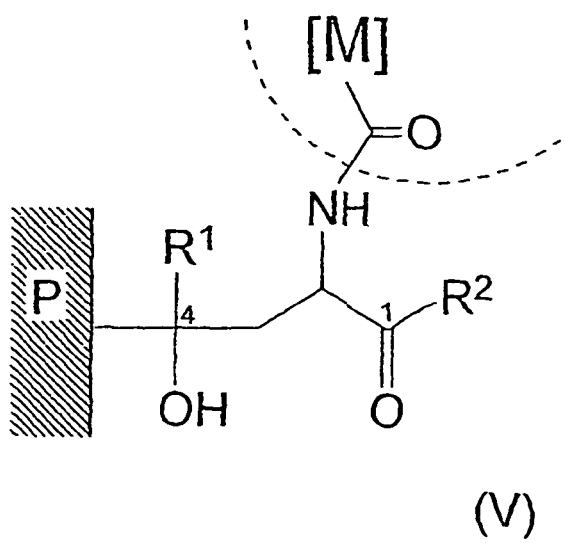

The peptide to be immobilized H-Ala-Ala-OH was combined as the alanylalanine methyl ester hydrochloride 2 (7.2 g) with 10 g of L-N-Boc-2-(2-oxo-2-phenylethyl) glycine 1, i.e., with a linker compound of the general formula (I) (compare FIGS. 1, 3), with $R^1$=phenyl, $R^2$=$OR^4$, $R^3$=t-butoxycarbonyl (Boc) and $R^4$=H, and 12 g of O-(benzotriazol-1-yl)-N,N, N',N'-tetramethyluronium tetrafluoroborate in 300 ml of dichloromethane.

Ethyl diisopropylamine (1.3 ml) was slowly dripped into this suspension while stirring at 0° C. (ice cooling). The suspension was heated to room temperature and stirring was continued, until compound 1 could still be detected only in trace amounts, by thin-layer chromatography (silica gel 60 F254, mobile phase: dichloromethane/methanol 10:1) (approximately 2 h). The mixture was placed in a separatory funnel and the organic phase was extracted sequentially with 500 ml each of water, saturated tartaric acid solution and saturated sodium hydrogen carbonate solution. The organic phase was separated, dried with sodium sulfate, and the solvent was removed on the rotary evaporator. Approximately 15 g of a resin were obtained, which were purified on silica gel 60 (mobile phase: dichloromethane/methanol 5:1) by flash column chromatography. The yield of 2-[2-(2-tert-butoxycarbonylamino-4-oxo-4-phenyl-butyrylamino)propionylamino] propionic acid methyl ester 3 (Boc-BzAla-Ala-Ala-OMe) amounted to 13 g.

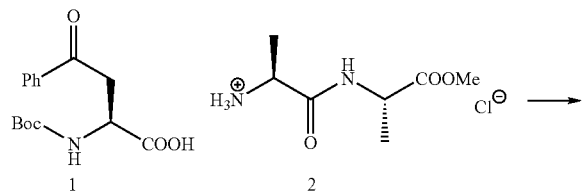

-continued

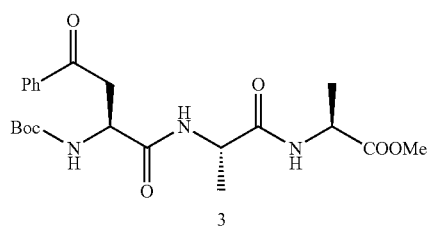

A polypropylene membrane (diameter 30 mm) was immersed for 30 minutes in a 0.1 M solution of 2-[2-(2-tert-butoxycarbonylamino-4-oxo-4-phenylbutyrylamino)propionylamino]propionic acid methyl ester 3, i.e., a photoreactive amino acid of the general formula (II) (compare FIG. 3), with $R^1$=phenyl, and $R^3$=t-butoxycarbonyl (Boc), and peptide H-Ala-Ala-OH bound to the N terminal as the methyl ester, as biomolecule M in dichloromethane, and then dried in high vacuum at $3 \cdot 10^{-5}$ Torr for 30 minutes.

The membrane was irradiated for 30 minutes with the light of an HBO 500 at a distance of 20 cm with the use of a cutoff filter, which filters out light below 290 nm.

The membrane was then washed five times with a total of 150 ml of dichloromethane and dried for 30 minutes in high vacuum at $3 \cdot 10^{-5}$ Torr.

The immobilization of the peptide according to formula (IV), in which the radicals $R^1$ und $R^3$ and the biomolecule M have the above-named meanings, was detected by comparison of the FT-IR spectra for the polypropylene membrane before and after treatment.

EXAMPLE 2

A polypropylene membrane (diameter 30 mm) was irradiated in a glass dish, filled with a 0.1 M solution of 2-[2-(2-tert-butoxycarbonylamino-4-oxo-4-phenylbutyrylamino) propionylamino]propionic acid methyl ester 3 (produced according to Example 1), i.e., a photoreactive amino acid of the general formula (II), with $R^1$=phenyl and $R^3$=t-butoxycarbonyl (Boc), and peptide H-Ala-Ala-OH bound to the N terminal as the methyl ester in benzene, for 60 minutes with the light of an HBO 500 at a distance of 20 cm with the use of a tilted mirror and a cutoff filter, which filters out light below 290 nm.

The membrane was then washed once with 50 ml of benzene and twice with 50 ml of dichloromethane and dried for 30 minutes in high vacuum at $3 \cdot 10^{-5}$ Torr.

The immobilization of the peptide according to formula (IV), in which the radicals $R^1$ and $R^3$ have the above-named meanings, was detected by comparison of the FT-IR spectra for the polypropylene membrane before and after treatment.

The invention claimed is:

1. A functionalized carrier material with a polymeric surface and at least one biomolecule covalently bound to the surface via a linker compound, wherein said functionalized carrier material has the general formula (IV) or (V):

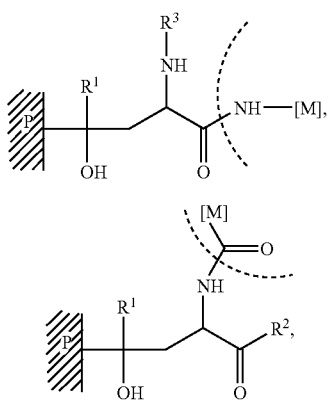

in which P indicates the polymeric surface of the carrier material and M indicates the biomolecule bound to the linker compound via an amino group (formula IV) or a carbonyl group (formula V) and $R^2$ of the linker compound has the meaning $OR^4$ or $NR^4R^5$; $R^1$, $R^4$ and $R^5$ of the linker compound, independently of one another, indicate H, an alkyl group or an aryl group; $R^3$ of the linker compound indicates H, an alkyl, an aryl, an acyl, an alkoxycarbonyl or an aryloxycarbonyl group; and the alkyl, aryl, acyl, alkoxycarbonyl and/or aryloxycarbonyl group indicated by $R^1$, $R^3$, $R^4$ and $R^5$, independently of one another, are substituted or unsubstituted.

2. The functionalized carrier material according to claim 1, wherein the biomolecule (M) is an amino acid, a peptide, a protein or a molecule with at least one peptidic structural unit.

3. The functionalized carrier material according to claim 1, wherein an organic polymer is used as the carrier material.

4. The functionalized carrier material according to claim 3, wherein the organic polymer is polypropylene, polyethylene, polysulfone, polyether sulfone, polystyrene, polyvinyl chloride, polyacrylonitrile, cellulose, arnylose, agarose, polyamide, polyimide, polytetrafluoroethylene, polyvinylidene difluoride, polyester, polycarbonate, polyacrylate, polyacrylamide or a derivative thereof or a copolymer or a blend of these.

5. The functionalized carrier material according to claim 1, wherein an inorganic and/or mineral material is used as the carrier material.

6. The functionalized carrier material according to claim 5, wherein a glass, a silicate, a ceramic material or a metal is used as the carrier material.

7. The functionalized carrier material according to one of claims 3 to 6, wherein a composite comprised of at least one inorganic and/or mineral material and at least one organic polymer is used as the carrier material.

8. The functionalized carrier material according to claim 1, wherein the carrier material is utilized in the form of a membrane, a film, a plate, a microtiter plate, a test tube, a glass slide, a fiber, a hollow fiber, a nonwoven material, a woven fabric, a powder, a granulate or particles, and the carrier material is porous or nonporous.

9. The functionalized carrier material according to claim 8, wherein the carrier material is utilized in the form of a membrane with a symmetric or asymmetric pore structure.

10. The functionalized carrier material according to claim 9, wherein the porous carrier material has a pore size of 1 nm to 10 μm.

* * * * *